United States Patent [19]
Yamato et al.

[11] Patent Number: 5,885,229
[45] Date of Patent: Mar. 23, 1999

[54] WALKING PATTERN PROCESSING METHOD AND SYSTEM FOR EMBODYING THE SAME

[75] Inventors: Junji Yamato; Kyoko Sudo; Akira Tomono, all of Kanagawaken; Masanobu Arai, Tokyo, all of Japan

[73] Assignee: Nippon Telegraph & Telephone Corp., Tokyo, Japan

[21] Appl. No.: 684,676

[22] Filed: Jul. 19, 1996

[30] Foreign Application Priority Data

Jul. 19, 1995 [JP] Japan ................................ 7-182984

[51] Int. Cl.⁶ .................................................. A61B 5/103
[52] U.S. Cl. ........................................... 600/592; 600/587
[58] Field of Search .................................. 600/587, 592, 600/595

[56] References Cited

U.S. PATENT DOCUMENTS

| | | | |
|---|---|---|---|
| 4,195,643 | 4/1980 | Pratt, Jr. .................................. | 128/779 |
| 4,267,728 | 5/1981 | Manley . | |
| 5,299,454 | 4/1994 | Fuglewicz et al. . | |
| 5,474,087 | 12/1995 | Nashner . | |
| 5,623,944 | 4/1997 | Nashner .................................. | 128/779 |

FOREIGN PATENT DOCUMENTS

| | | |
|---|---|---|
| 2-55045 | 2/1990 | Japan . |
| 3-55077 | 3/1991 | Japan . |
| 3-212263 | 9/1991 | Japan . |
| 3-247304 | 11/1991 | Japan . |

OTHER PUBLICATIONS

Article from *Technical Report of IEICE*, Person Identification by Footstep Pressure Images Captured by Large Area Pressure Sensor Array:, Yamato, et al., pp. 15–22, and English abstract thereof.

*Krusen's Handbook of Physical Medicine and Rehabilitation*, Fourth Edition, 1990, Kotte, M.D. and Lehmann, M.D., pp. 108–114.

*Primary Examiner*—Max Hindenburg
*Assistant Examiner*—Pamela L. Wingood
*Attorney, Agent, or Firm*—Banner & Witcoff Ltd

[57] ABSTRACT

According to the present invention, two-dimensional pressure distribution associated with walking are collected at a preselected time interval as time series pressure distribution images, superposed images are formed by superposing the time series pressure distribution images in a time direction, a plurality of foot pressure mass regions are extracted from the superposed images, correspondence of each foot pressure mass region to the time series pressure distribution images are detected, feature parameters associated with the walking are detected based on the correspondence, and the feature parameters are displayed or printed.

18 Claims, 13 Drawing Sheets

FIG.8A    FIG.8B
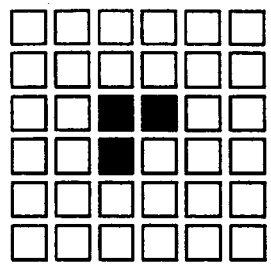 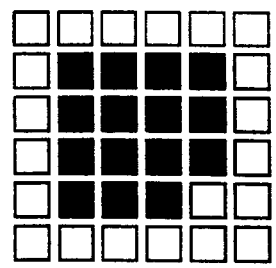
FIG.8C    FIG.8D    FIG.8E
 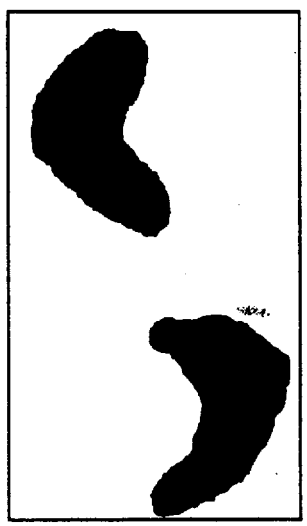 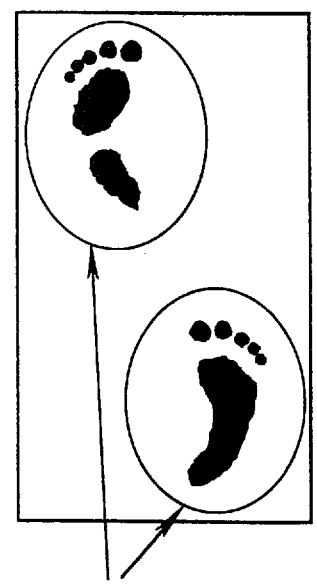
FOOTPRINT REGION EVERY STEP

WALKING PATTERN PROCESSING METHOD AND SYSTEM FOR EMBODYING THE SAME

BACKGROUND OF THE INVENTION

1. Field of the Invention

The present invention relates to a walking pattern processing method and a system for embodying the same and, more particularly, a walking pattern processing method of measuring human walking actions, analyzing the results of measurement, and displaying them as parameters and a system for embodying the same.

2. Description of the Prior Art

Conventionally, there has been two means as means for analyzing and processing walking patterns, i.e., means using a force plate and means using a pressure distribution sensor in foot size.

According to the means using the force plate, force change in walking can be measured in time series. However, neither pressure distribution in a foot contact region of foot, nor foot contact location in walking can be measured.

Alternatively, according to the means using the pressure distribution sensor in foot size, if the inner bottom of shoes is covered with the pressure distribution sensor in foot size, not only pressure distribution in the footmark can be measured, but also respective instants of foot contact and heel off can be measured. However, location of foot contact in walking cannot be measured.

As a method of measuring location of foot contact, there have been merely troublesome measuring methods such as method of walking with inked feet on the sheet to then measure location of foot contact, method of taking a video of walking together with scale and then measuring location of foot contact while reproducing the video, or the like.

Likewise, as a method of displaying the results of analysis of walking patterns in the prior art, there have been several methods such as direct display of respective parameter values, statistical display thereof, etc. However, it has been difficult to accumulate a great deal of data because of their insufficient measuring methods. Accordingly, no display method by which a large amount of data are able to be easily grasped has not developed yet. Furthermore, as a conventional display method of common walking parameters, there have been display methods, e.g., those shown in FIGS. 1 and 2. However, since both figures are only for use in conceptual explanations, there is given no means for implementing such display methods equivalent to these figures to display the actual measured and analyzed results.

As explained previously, there has been a problem that it is difficult for the conventional analyzing method to display parameters associated with location and time of foot contact simultaneously and simply. Furthermore, as for display of the measured results, there has been another problem that, if the walking action which is taken as a time series phenomenon performed in three-dimensional space is depicted on the two-dimensional paper either by a few parameters or as the schematic view, such walking action would be hard to be understood intuitively and also would require a great amount of skill to be grasped.

SUMMARY OF THE INVENTION

The present invention has been made in light of the above circumstances, and an object of the present invention is to provide a walking pattern processing method capable of collecting spatial and time parameters concerning walking actions automatically, stably, and simply without imposing a heavy burden on a subject and also facilitating intuitive understanding and quantitative comparison of spatial and time factors of walking actions and a system for embodying the same.

In order to attain the above object, according to an aspect of the present invention, there is provided a walking pattern processing system comprising: a pressure sensor for acquiring two-dimensional pressure distribution associated with walking; time series pressure distribution image detecting means for collecting output from the pressure sensor at a preselected time interval as time series pressure distribution images; superposed image forming means for forming superposed images by superposing the time series pressure distribution images in a time direction; foot pressure mass region picking-out means for extracting a plurality of foot pressure mass regions from the superposed images; step correspondence detecting means for detecting correspondence of each foot pressure mass region to the time series pressure distribution images; parameter detecting means for detecting feature parameters of the walking based on the correspondence detected by the step correspondence detecting means; and outputting means for outputting the parameters.

According to the present invention, since walking parameters are collected from two-dimensional pressure distribution acquired in time series and their superposed images, basic parameters associated with walking can be obtained automatically and simply. In addition, intuitive understanding of walking pattern can be achieved based on foot pressure mass patterns on the superposed images, and therefore understanding, comparison, and recording of the walking patterns which require a great deal of skill in the prior art can be facilitated.

In the preferred embodiment, the parameter detecting means includes feature location detecting means for detecting predetermined feature locations from the superposed images based on the correspondence detected by the step correspondence detecting means.

In the preferred embodiment, the predetermined feature locations are rear end portion, front end portion, portion which came into contact with the pressure sensor first, center, and center of gravity of each foot pressure mass relative to a walking direction.

In the preferred embodiment, the parameter detecting means includes, initial frame detecting means for detecting a frame having a pressure value firstly relative to each foot pressure mass region based on the correspondence detected by the step correspondence detecting means, final frame detecting means for detecting a frame having a pressure value finally relative to each foot pressure mass region based on the correspondence detected by the step correspondence detecting means, and time interval detecting means for detecting time parameters based on time information associated with respective frames detected by the initial frame detecting means and the final frame detecting means.

In the preferred embodiment, the parameter detecting means includes center of gravity location detecting means for detecting center of gravity of pressure values relative to each pressure distribution image based on the correspondence detected by the step correspondence detecting means.

In the preferred embodiment, the parameter detecting means includes moving direction detecting means for detecting a direction in which the center of gravity moves in a time direction, based on the center of gravity of the pressure values relative to each pressure distribution image detected by the center of gravity location detecting means.

In the preferred embodiment, the foot pressure mass region picking-out means magnifies regions containing pixel values by certain pixels upon extracting each foot pressure mass, and then regards such regions superposed with each other upon being magnified as footprint region in the same step.

According to this embodiment, respective steps can be extracted precisely from the superposed images associated with plural steps.

According to another aspect of the present invention, there is provided a walking pattern processing method comprising the steps of: collecting two-dimensional pressure distribution associated with walking at a preselected time interval as time series pressure distribution images; forming superposed images by superposing the time series pressure distribution images in a time direction; extracting a plurality of foot pressure mass regions from the superposed images; detecting correspondence of each foot pressure mass region to the time series pressure distribution images; detecting feature parameters associated with the walking based on the correspondence; and displaying or printing the feature parameters.

In the preferred embodiment, rear end portion, front end portion, and center in each step are detected as the feature parameters, information as to a stride duration and a step duration are displayed or printed in parallel to and in registration with to the superposed images, and information as to a step width are displayed or printed so as to overlap with the superposed images.

According to this embodiment, magnitude of respective parameters of stride length, step length, and step width can be grasped as a whole.

In the preferred embodiment, locations of the center of gravity of pressure values in each pressure distribution image are detected as the feature parameters, and detected locations of the center of gravity of pressure values in each pressure distribution image are displayed or printed in parallel to the superposed images.

According to this embodiment, since movement of the center of gravity is displayed or printed, dynamic speed variation can be grasped readily.

In the preferred embodiment, moving direction of the locations are detected upon detecting the locations of center of gravity of pressure values, and displaying or printing process is inverted if the center of gravity moves in a direction opposite to walking direction.

According to this embodiment, abnormality in movement of the center of gravity can be easily found.

In the preferred embodiment, the center of gravity of pressure distribution images having a pressure value firstly in each step is detected as the feature parameters, and location of the center of gravity is displayed or printed so as to overlap with the superposed images.

According to this embodiment, such abnormal walking can be easily found that tiptoe is contacted first in place of heel on foot contact.

In the preferred embodiment, stride duration, step duration, double stance duration, and swing duration are detected as the feature parameters, and foot contact times on both feet in connection with the stride duration, the step duration, the double stance duration, and the swing duration are displayed or printed by respective line segments along a time axis.

According to this embodiment, time parameters are capable of being grasped easily.

In the preferred embodiment, sum total or an average value of the pressure values at respective time points is displayed or printed in different color or with different density so as to overlap with the line segments.

According to this embodiment, association of change in foot pressure in a time direction with walking action can be understood with ease.

In the preferred embodiment, stride length, step length, step width, stride duration, step duration, double stance duration, and swing duration are detected as the feature parameters, and the stride length, the step length, the step width, the stride duration, the step duration, the double stance duration, and the swing duration are displayed or printed in scale so as to collate a right foot and a left foot with each other.

According to this embodiment, a degree of important difference between right and left feet in abnormal walking can be found readily, and at the same time it can be determined easily whether such difference between right and left feet is irregular or not by comparing magnitudes of difference between right and left feet.

In the preferred embodiment, data concerning the stride length, the step length, the step width, the stride duration, the step duration, the double stance duration, and the swing duration are displayed or printed respectively, and average values, values of average value±standard deviation, maximum values and minimum values of these data are displayed or printed in different colors to overlap with the data.

According to this embodiment, a degree of variation of plural times which is important for abnormal walking is facilitated, and simultaneously it can be determined easily whether such difference between right and left feet is irregular or not by comparing magnitudes of difference between right and left feet.

In the preferred embodiment, stride length, step length, and step width are detected as the feature parameters, and the stride length, the step length, and the step width are displayed or printed as a radar chart.

In the preferred embodiment, the step length and the stride length which are lengths in a walking direction are selected as vertical parameters in the radar chart, and the step width which is a length in a direction perpendicular to the walking direction is selected as a lateral parameter in the radar chart, and respective parameters on right and left feet are arranged correspondingly on right and left sides of the radar chart.

According to this embodiment, balance of respective spatial parameters and their right and left balance can be understood intuitively.

In the preferred embodiment, stride duration, step duration, double stance duration, and swing duration are detected as the feature parameters, and the stride duration, the step duration, the double stance duration, and the swing duration are displayed or printed as a radar chart.

In the preferred embodiment, time required for step and stride actions in a walking direction are selected as vertical parameters in the radar chart, and the double stance duration and the swing duration on a right foot and a left foot are selected as lateral parameters in the radar chart, and respective parameters on right and left feet are arranged correspondingly on right and left sides of the radar chart.

According to this embodiment, balance of respective spatial parameters and their right and left balance can be grasped intuitively.

The nature, principle and utility of the invention will become more apparent from the following detailed description when read in conjunction with the accompanying drawings.

BRIEF DESCRIPTION OF THE DRAWINGS

In the accompanying drawings:

FIGS. 8A to 8E are views illustrating process to pick out regions which are regarded as a footprint in the same step on superposed image as foot pressure mass region;

DESCRIPTION OF THE PREFERRED EMBODIMENTS

Preferred embodiments of the present invention will be explained in detail with reference to accompanying drawings hereinafter.

Figure 1:
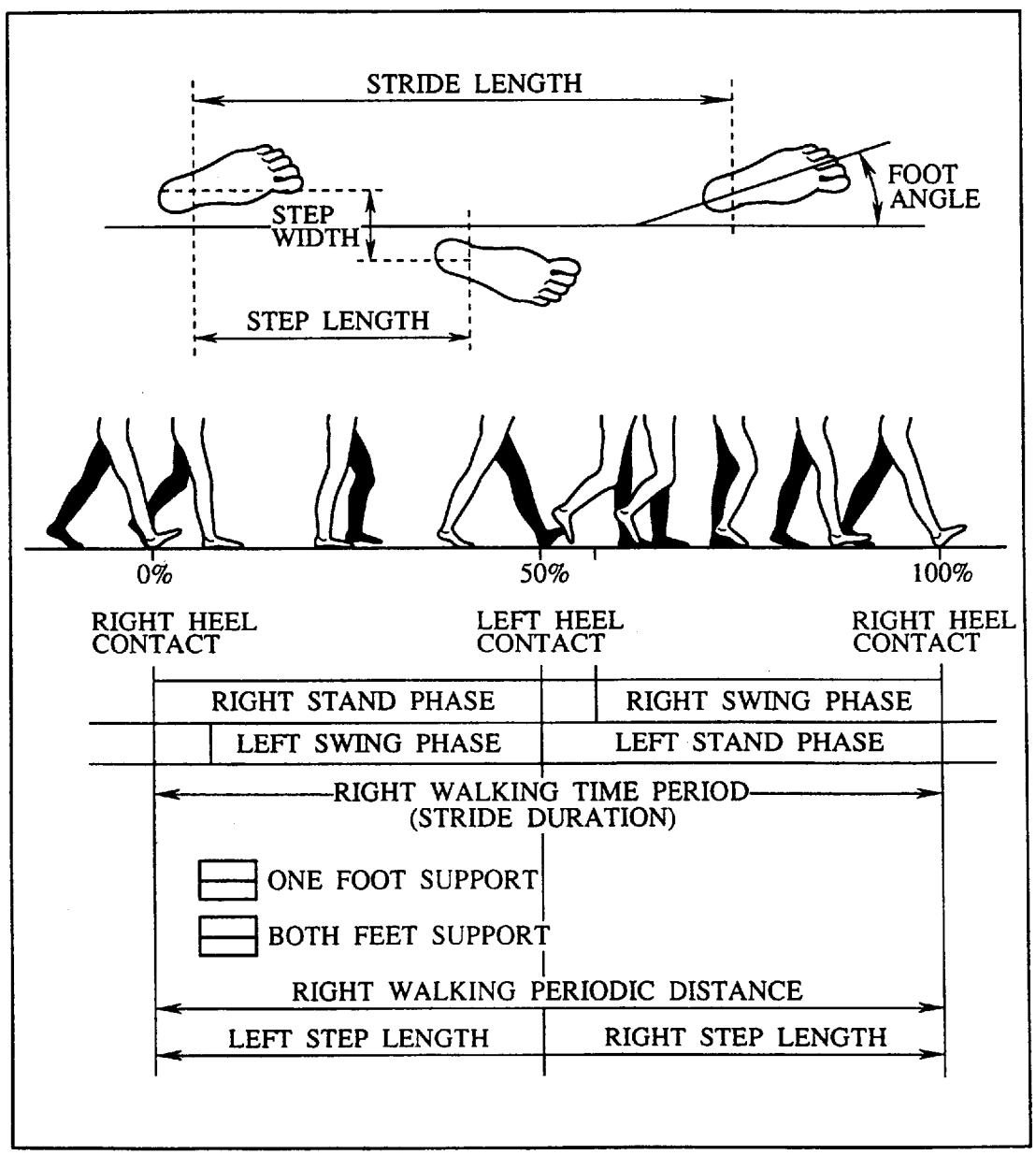
FIG. 1 is a diagrammatic view illustrating a method of displaying walking parameters in the prior art.
Figure 2:
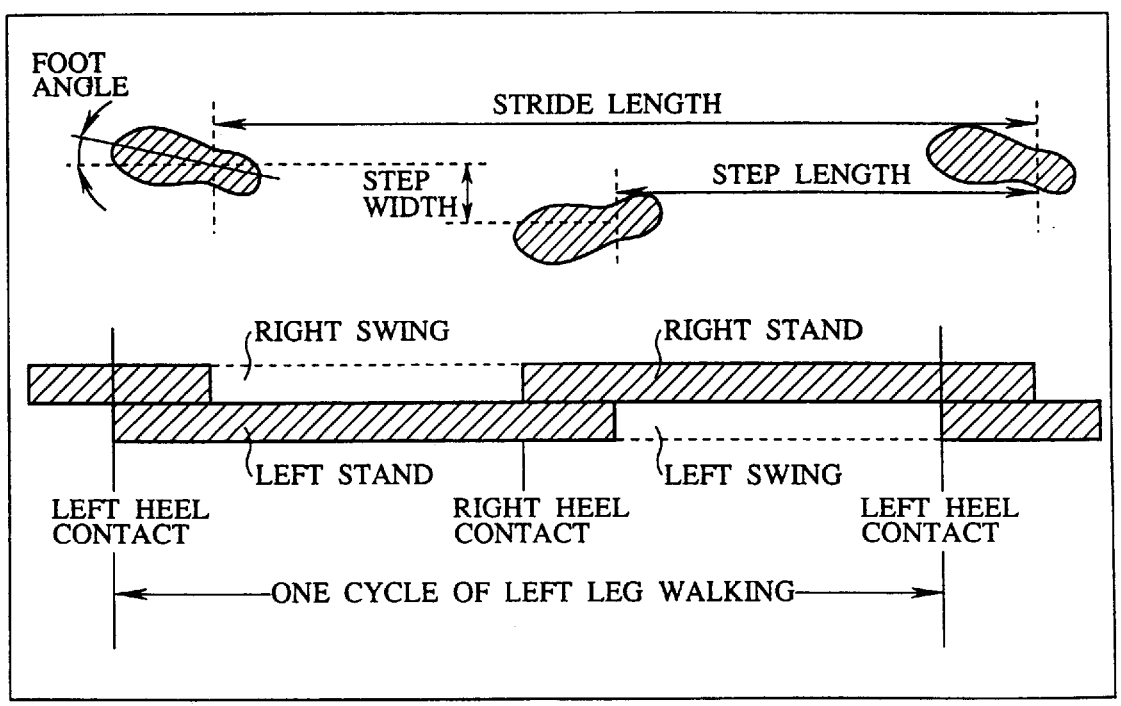
FIG. 2 is a diagrammatic view illustrating another method of displaying walking parameters in the prior art.
Figure 3:
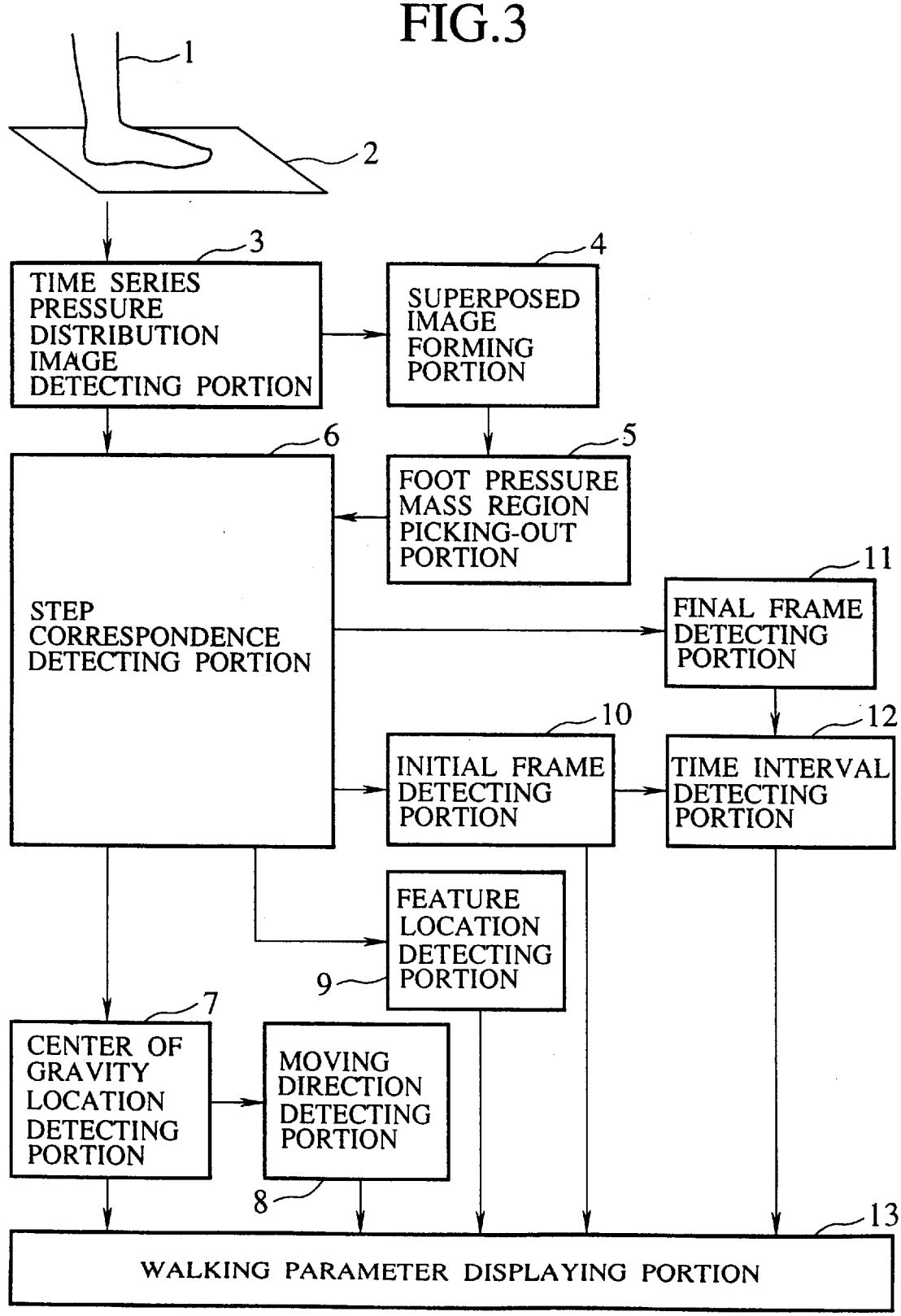
FIG. 3 is a block diagram showing a configuration of a walking pattern processing system according to an embodiment of the present invention.

FIG. 3 is a block diagram showing a configuration of a walking pattern processing system according to an embodiment of the present invention. In FIG. 3, a reference 1 denotes a foot of a walker; 2, pressure sensor for acquiring two-dimensional pressure distribution; 3, time series pressure distribution image detecting portion for collecting output from the pressure sensor 2 at a preselected time interval as time series data; 4, a superposed image forming portion for superposing the time series pressure distribution images in a time direction; 5, foot pressure mass region picking-out portion for extracting foot pressure mass regions from the superposed images; 6, step correspondence detecting portion for detecting correspondence of the foot pressure mass images to the time series image sequence every step by searching the foot pressure mass images; 7, center of gravity location detecting portion for detecting location of center of gravity in the time series image sequence; 8, moving direction detecting portion for detecting moving direction of the center of gravity location sequence; 9, feature location detecting portion for detecting feature locations of respective images after being correlated in the step correspondence detecting portion 6; 10, initial frame detecting portion for detecting an initial frame out of steps of respective images after being correlated in the step correspondence detecting portion 6; 11, final frame detecting portion for detecting a final frame out of steps of respective images after being correlated in the step correspondence detecting portion 6; 12, time interval detecting portion for detecting time intervals between the initial frame and the final frame; and 13, walking parameter displaying portion for displaying respective walking parameters.

Figure 4:
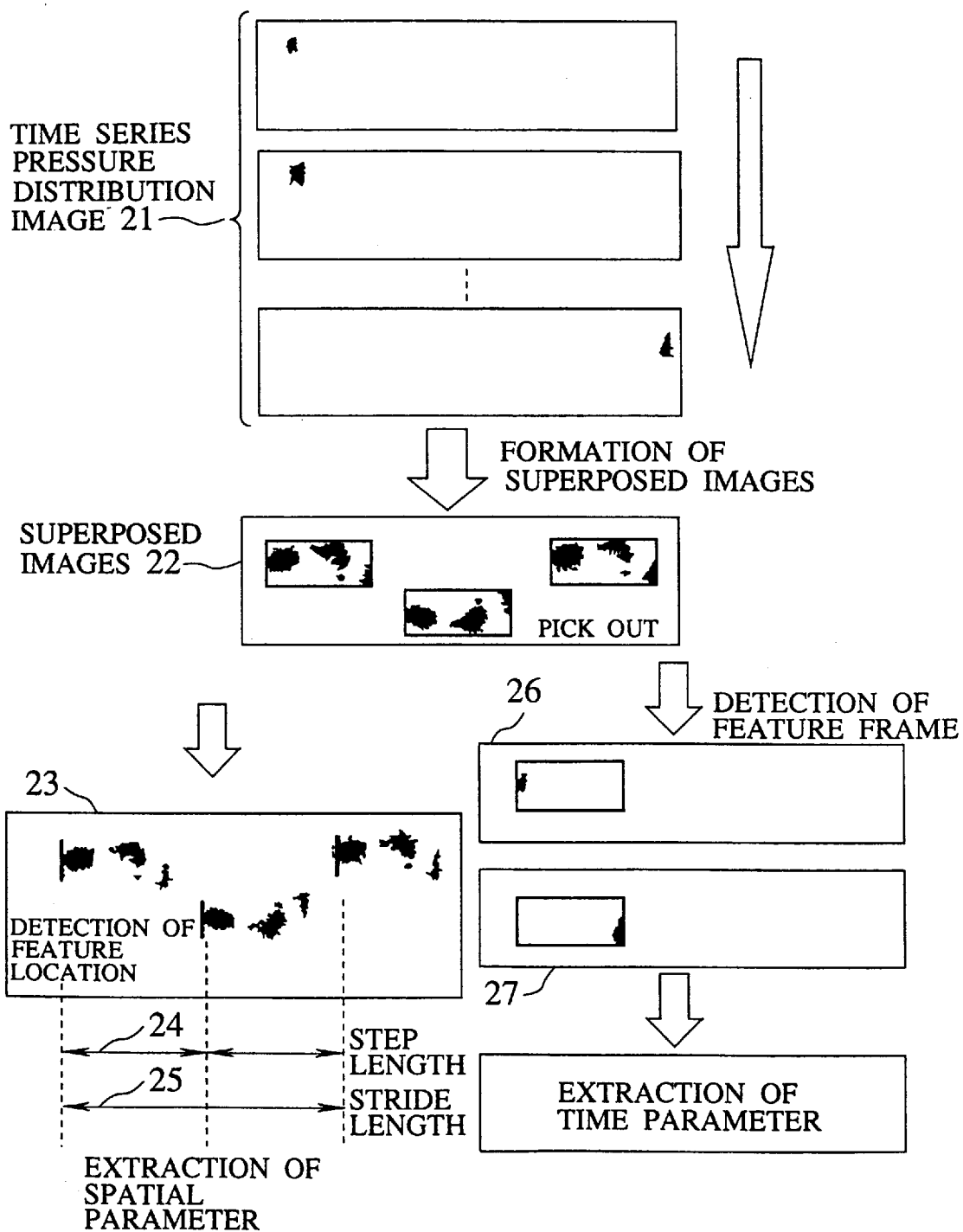
FIG. 4 is a view illustrating a flow of processing of pressure distribution images by the walking pattern processing system shown in FIG. 3.

FIG. 4 is a view illustrating a flow of processing of pressure distribution images by the walking pattern processing system shown in FIG. 3. In FIG. 4, a reference 21 denotes time series pressure distribution images being collected; 22, superposed image, and a square frame in this superposed image corresponds to a foot pressure image mass region in one step; and 23, displayed image on which feature points are superposed on the superposed images. A reference 24 denotes a step length measured on the image 23; and 25, stride length measure on the image 23. References 26, 27 denote an initial frame and a final frame of the same foot pressure image mass region, respectively.

Figure 5:
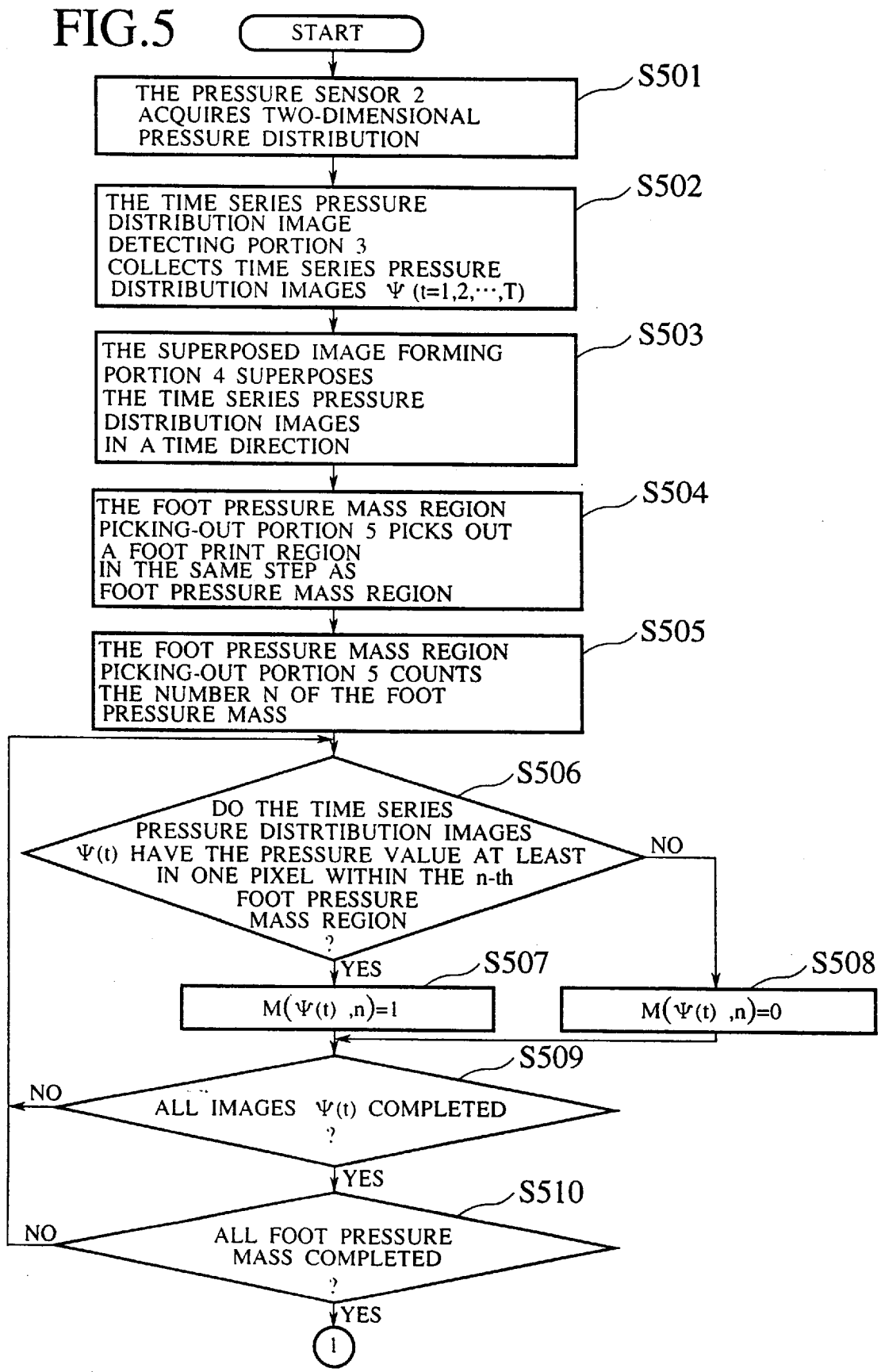
FIG. 5 is a flowchart illustrating the details of processing of pressure distribution image.
Figure 6:
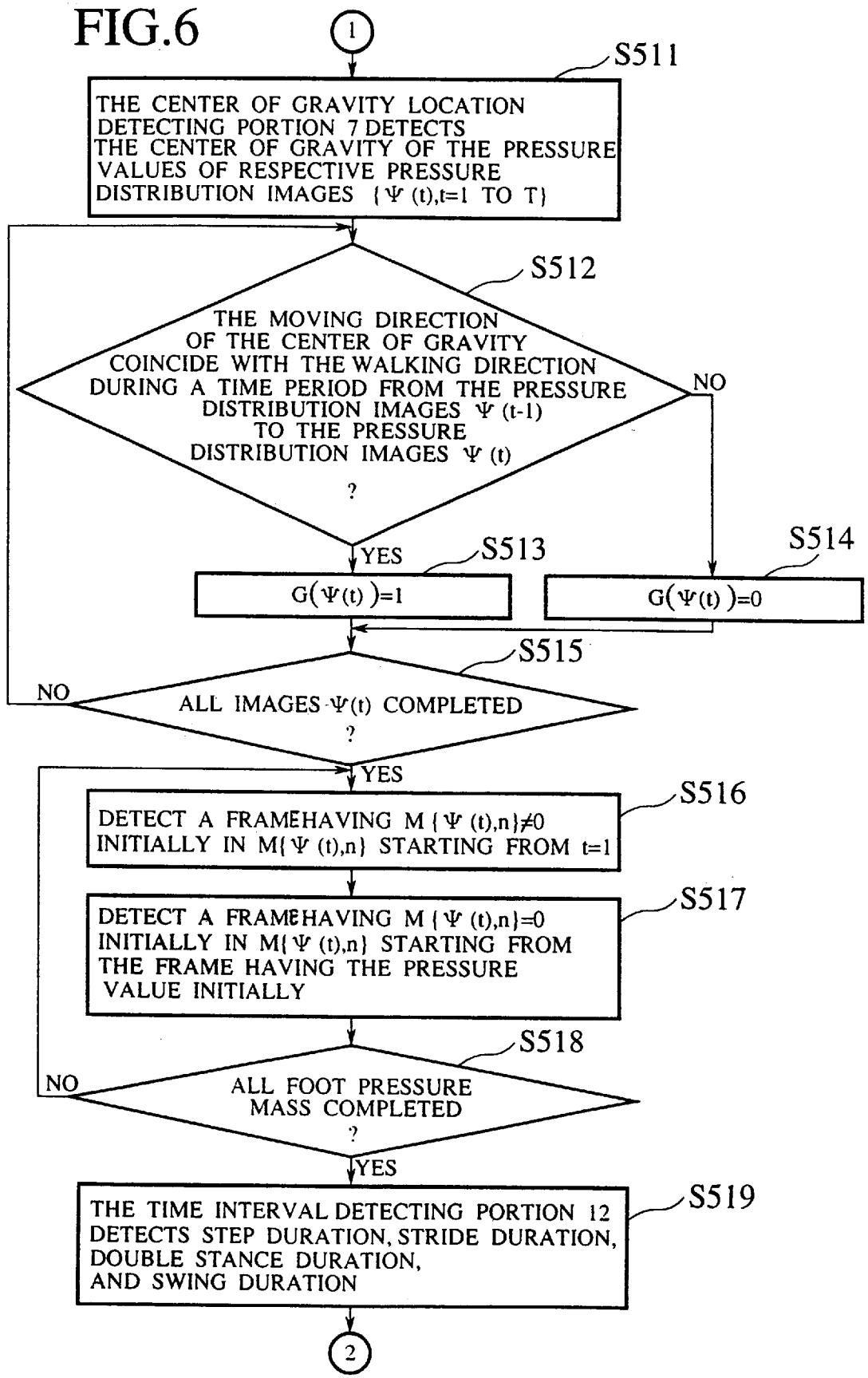
FIG. 6 is a flowchart illustrating the details of processing of pressure distribution image.
Figure 7:
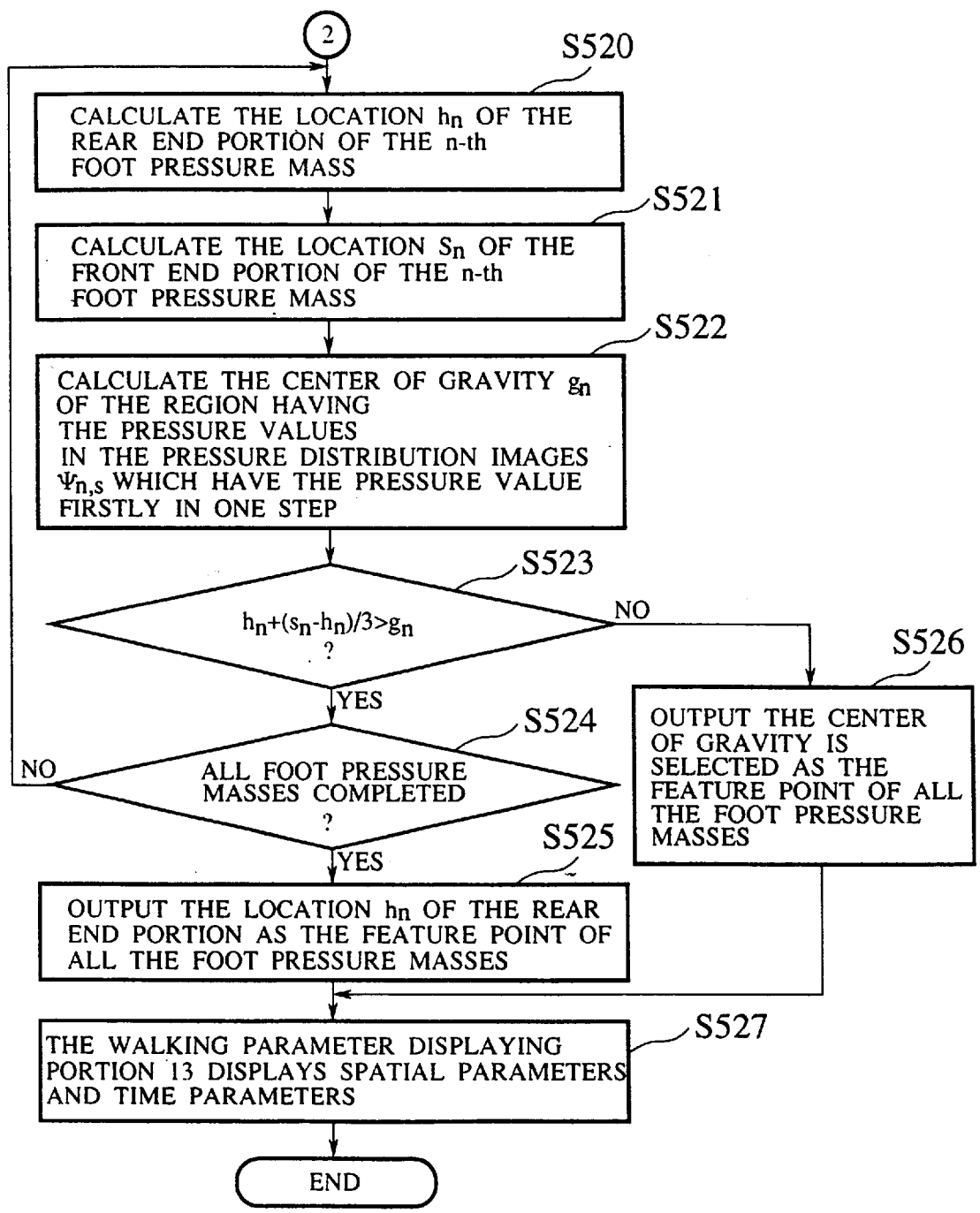
FIG. 7 is a flowchart illustrating the details of processing of pressure distribution image.

FIGS. 5, 6 and 7 are flowcharts illustrating the details of processing of pressure distribution image. The details will be explained with reference to FIGS. 5, 6 and 7 in the following.

First the foot 1 moves on the pressure sensor 2. In this event, the pressure sensor 2 may acquire two-dimensional unique pressure distribution generated by the walking pattern of the foot 1 (step S501). In other words, the pressure sensor 2 may acquire pressure value outputs corresponding to the coordinate values associated with the pressure sensor 2.

The time series pressure distribution image detecting portion 3 may detect two-dimensional pressure distribution pattern which being acquired by the pressure sensor 2 continuously at a preselected time interval for a certain time period, and collects T sheets of time series pressure distribution images $\psi$ (t=1, 2, ..., T) (step S502). It is preferable that this preselected time interval is in the range of $\frac{1}{10}$ sec to $\frac{1}{100}$ sec. For instance, in case measurement is performed at a $\frac{1}{10}$ time interval for 5 seconds, 50 sheets of time series pressure distribution images numbered as t=1 to 50 respectively can be collected.

The superposed image forming portion 4 may superpose in a time direction the time series pressure distribution images which are collected by the time series pressure distribution image detecting portion 3 (step S503). In this superposing processing, two processing methods explained in the following will be effectively available. One is that the maximum value of the pressure value outputs from the pressure sensors is used as the value serving as the superposed images in the corresponding location to the sensor, and the other is that total sum of the pressure value outputs from the pressure sensors is also used as the value serving as the superposed images in the corresponding location to the sensor.

The foot pressure mass region picking-out portion 5 may pick out, as foot pressure mass region, regions which are regarded as a footprint in the same step on the superposed images (step S504). At this time, there is no trouble to regard adjacent pixels each having a certain value on the superposed images as the regions located in the same step. However, since there is a case where, like respective foot fingers, the same step may appear as discrete regions on the pressure distribution images, the following process will be available.

Specifically, regions in the superposed images in which pixels have certain values respectively are magnified by one pixel to ten pixel areas, and then such regions being superposed upon magnification are regarded as the footprint region in the same step. As shown in FIGS. 8A and 8B, the process for magnifying the regions can be accomplished by including neighboring pixels in the region into the same region. FIG. 8A is a view illustrating an original image, while FIG. 8B is a view illustrating an image obtained according to the magnification process by one pixel, for purposes of example. More particularly, assume that the original image shown in FIG. 8C has been obtained, for example. The image shown in FIG. 8D can be derived by the magnification process. By considering the continuous pixel regions having values in FIG. 8D as the footprint region in the same step and then picking out the corresponding regions from FIG. 8C, the footprint regions in the superposed images can be obtained every step, as shown in FIG. 8E.

Since a profile of the footprint region is close to a rectangle shape which is prolonged in the walking direction, it is available to alter a magnification ratio in response to respective directions in the magnification process shown in FIG. 8B. For instance, ten pixel areas are magnified in a walking direction and five pixel areas are magnified in a direction perpendicular to the walking direction. According to this process, even if right and left footprints appear closely in the superposed images, footprints can be picked out stably.

In addition, it is effective to have an interface which enables the operator to designate the footprint in the same step interactively by visually watching the superposed image by operator's eyes.

The foot pressure mass region picking-out portion 5 may also count the number N of the foot pressure mass (step S505).

Subsequently, the step correspondence detecting portion 6, for respective steps picked out from the foot pressure mass region picking-out portion 5, may search the time series pressure distribution images from t=1, and detect the time series pressure distribution images having the pressure value at least in one pixel in the step region (step S506 to step S510). In other words, for example, an array $M(\psi(t), n)$ is prepared. Where n denotes a parameter for specifying the n-th step. M is set to 1 for the time series pressure distribution images having the pressure value in at least one pixel (step S507), otherwise M is set to M=0. In fact, for purposes of example, the array $M(\psi(t), n)$ is set like $M(\psi(5), 1)$–$M(\psi(25), 1)=1$, $M(\psi(20), 2)$–$M(\psi(40), 2)=1$, $M(\psi(35), 3)$–$M(\psi(55), 3)=1, \ldots$.

The center of gravity location detecting portion 7 may detect the center of gravity of the pressure values of respective pressure distribution images $\{\psi(t), t=1{\sim}T\}$ (step S511). At this time, there are two kinds of object ranges to detect the center of gravity therein as follows. One is for the allover pressure images, i.e., pressure images associated with both feet, and the other is for the pressure images regarding each foot, i.e., independently for each foot.

The moving direction detecting portion 8 may detect moving direction of the center of gravity in a time direction based on the center of gravity of the pressure values in respective pressure distribution images which have been detected by the center of gravity location detecting portion 7 (step S512 to step S515). In other words, it is determined whether or not the center of gravity has moved in the pressure distribution images immediately before now in either the same direction as the walking direction or the opposite direction to the walking direction. For example, in the event that an array $G(\psi(t))$ is prepared, such array G is set as $G(\psi(t))=1$ when the moving direction of the center of gravity coincides with the walking direction during the movement from the pressure distribution images $\psi(t-1)$ to the pressure distribution images $\psi(t)$, and on the contrary such array G is set as $G(\psi(t))=1$ when the moving direction of the center of gravity is opposite to the walking direction during the same movement. The moving direction of the center of gravity may be detected also on either both feet or one foot.

The initial frame detecting portion 10 may detect a frame which has the pressure values initially in one step, i.e., pressure distribution image $\psi_{n,s}$ out of images in respective steps detected by the step correspondence detecting portion 6 (step S516). More particularly, after searching from t=1, a frame which provides $M(\psi(t), n) \neq 0$ initially is detected out of an array $M(\psi(t), n)$.

Then the final frame detecting portion 11 may detect a final frame which has the pressure values finally in one step, i.e., pressure distribution image $\psi_{n,e}$ out of images in respective steps detected by the step correspondence detecting portion 6 (step S517). More particularly, after starting the frame having the pressure value first, a frame which provides $M(\psi(t), n)=0$ firstly is detected.

Based on information detected by the initial frame detecting portion 10 and the final frame detecting portion 11, the time interval detecting portion 12 may detect time interval from starting of certain step to starting of succeeding step (step duration), time interval from starting of certain step of the right foot or left foot to starting of succeeding step of the left foot or right foot (stride duration), time interval required for foot contact action of both right and left feet (double stance duration), and time interval required for swing action of one right or left foot (swing duration) (step S519). More particularly, the step duration may be detected by multiplying (the number $(t_{n+1,s})$ of $\psi_{n+1,s}$-the number $(t_{n,s})$ of $\psi_{n,s}$) by frame time interval. The stride duration may be detected by multiplying (the number $(t_{n+2,s})$ of $\psi_{n+2,s}$-the number $(t_{n,s})$ of $\psi_{n,s}$) by frame time interval. The double stance duration may be detected by multiplying (the number $(t_{n+1,s})$ of $\psi_{n+1,s}$-the number $(t_{n,e})$ of $\psi_{n,e}$) by frame time interval. The swing duration may be detected by multiplying (the number $(t_{n+2,s})$ of $\psi_{n+2,s}$—the number $(t_{n,e})$ of $\psi_{n,e}$) by frame time interval.

The feature location detecting portion 9 may detect predetermined feature locations from the superposed images representing the footprint region in respective steps (step S520 to step S526). In the superposed images representing the footprint in respective steps, rear end portion, front end portion, portion which came into contact with the pressure sensor first, center, and center of gravity relative to the walking direction are available as such feature locations.

In the normal walking by the walker, location of the rear end portion can be detected most stably. However, in the abnormal walking in which foot contact is not done by heel in the first image in one step, there are some cases where location of the rear end portion cannot be detected stably. Therefore, unless the center of gravity of pressure distribution of the first image in the step is included in the one third backward region of the superposed images, the center or the center of gravity may be available in place of the rear end portion.

In particular, first the location $h_n$ of the rear end portion of the n-th foot pressure mass is calculated (step S520). The location sn of the front end portion of the n-th foot pressure mass is then calculated (step S521). In the pressure distribution images $\psi_{n,s}$ which are detected in step S516 and have the pressure value firstly in one step, the center of gravity $g_n$ of the region having the pressure values is calculated (step S522).

In turn, it is determined whether or not the equation (1) is satisfied (step S523).

$$h_n + (s_n - h_n)/3 > g_n \qquad (1)$$

In other words, it is determined whether or not the location which is away from the location $h_n$ of the rear end portion of the foot pressure mass by a distance of ⅓×(total length of the foot pressure mass) in the walking direction is located forwardly rather than the location of the center of gravity $g_n$. Allover foot pressure mass is determined (step S524). As a result, if decisions concerning allover foot pressure mass in step S523 are affirmative, the location $h_n$ of the rear end portion is selected as the feature point of all the foot pressure mass (step S525). On the other hand, if any of foot pressure mass in step S523 are decided negatively, the center of gravity is selected as the feature point of all the foot pressure mass (step S526).

The walking parameter displaying portion 13 may display information detected by the center of gravity location detecting portion 7, the moving direction detecting portion 8, the feature location detecting portion 9, the initial frame detecting portion 10, and the time interval detecting portion 12 on a display device so as to be recognized intuitively by the operator (step S527).

Figure 9:
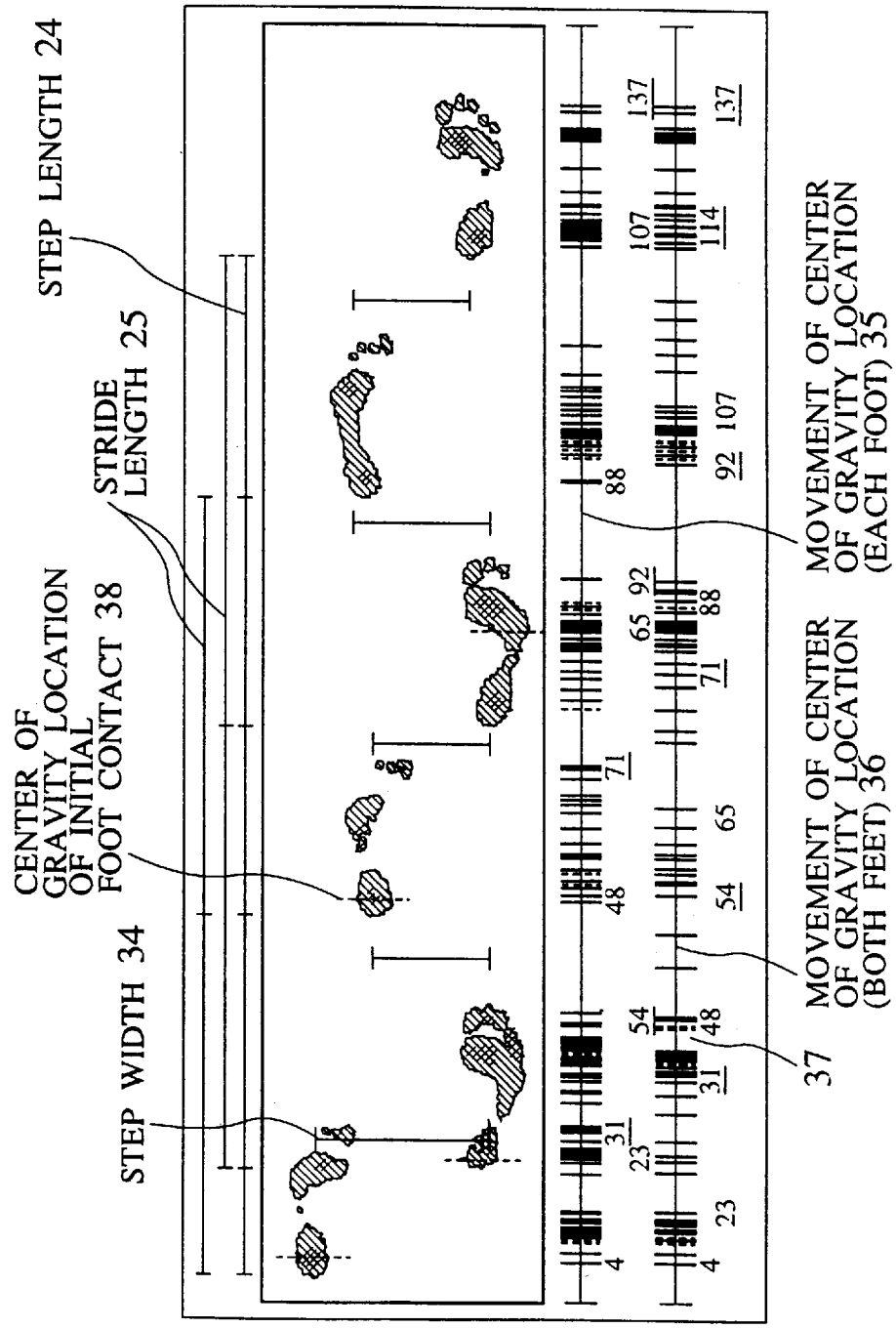
FIG. 9 is a view showing a screen on which superposed images, their movement of the center of gravity, and the like are displayed in parallel, i.e., a so-called spatial chart.

FIG. 9 is a view showing a screen on which superposed images, their movement of the center of gravity, and the like are displayed in parallel, i.e., a so-called spatial chart. The walking parameter displaying portion 13 may set a distance in the walking direction as a abscissa, and display the superposed images formed in step S503 in the center of the ordinate. The walking parameter displaying portion 13 may plot respective locations of the center of gravity of the time series pressure distribution images displayed by the center of gravity location detecting portion 7 in the lower display area provided below the superposed images. In this embodiment, both the movement of the center of gravity (one foot alone) 35 and the movement of the center of gravity (both feet) 36 are displayed. According to change in the moving direction detected in step S512 to step S515, display methods should be also changed in different moving directions in display of this movement of the center of gravity. For example, colors are changed or solid lines and broken lines are used to distinguish them. In this embodiment, the center of gravity is indicated by the broken line, as shown in the display 37, if it moves in the opposite direction. Different colors should be used on the actual screen for easy watching, for example, indication by blue color is used if the movement of the center of gravity movement is in the walking direction, and indication by red color is used if the movement of the center of gravity is in the opposite direction.

On the basis of information as to the rear end portion and the front end portion of respective steps detected by the feature location detecting portion 9, the walking parameter displaying portion 13 may display the step length 24 and the stride length 25 by horizontal lines in the upper display area provided over the superposed images. The step width 34 is also displayed by a vertical line segment so as to overlap with the superposed images. Where the step length is defined as a distance from the right foot to the left foot or vice versa in the walking direction. The stride length is termed as a distance from the right foot via the left foot to the right foot again or vice versa. The step width is defined as a distance between feature locations in the direction intersecting orthogonally with the walking direction.

The walking parameter displaying portion 13 may receive the location of the center of gravity of the initial frame detected by the initial frame detecting portion 10 from the center of gravity location detecting portion 7, and display it as the center of gravity location of initial foot contact 38 so as to overlap with the superposed images.

These unified display may not only be displayed but also printed as it is.

Figure 10:
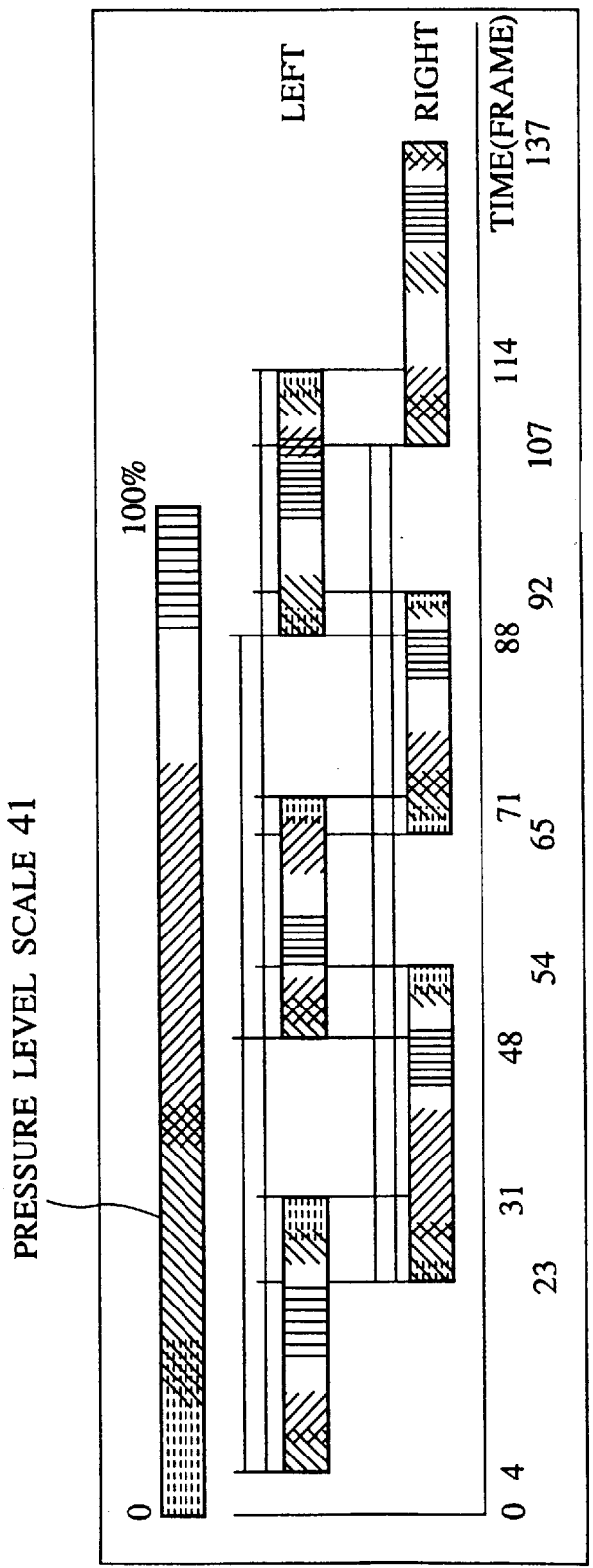
FIG. 10 is a view showing a display of time chart.

FIG. 10 is a view showing a display of time chart. The walking parameter displaying portion 13 sets walking time as the abscissa. The walking parameter displaying portion 13 receives respective time parameters from the time interval detecting portion 12, and displays respective time parameters by horizontal line segments separately on the same time axis when the walking being started from the left foot and started from the right foot. Upon this display, total sum or average value of the pressure values at respective time points may be displayed in different color or with different density of display. At this time, it is desired that pressure level scale 41 is displayed together. Since the pressure level has large individual difference, it is effective to change color or density scale of the pressure level every individual person with using the maximum value of the walker to be measured as a full scale. Preferably, in the pressure level scale, larger pressure level is displayed with reddish color and smaller pressure level is displayed with bluish color.

Figure 11:
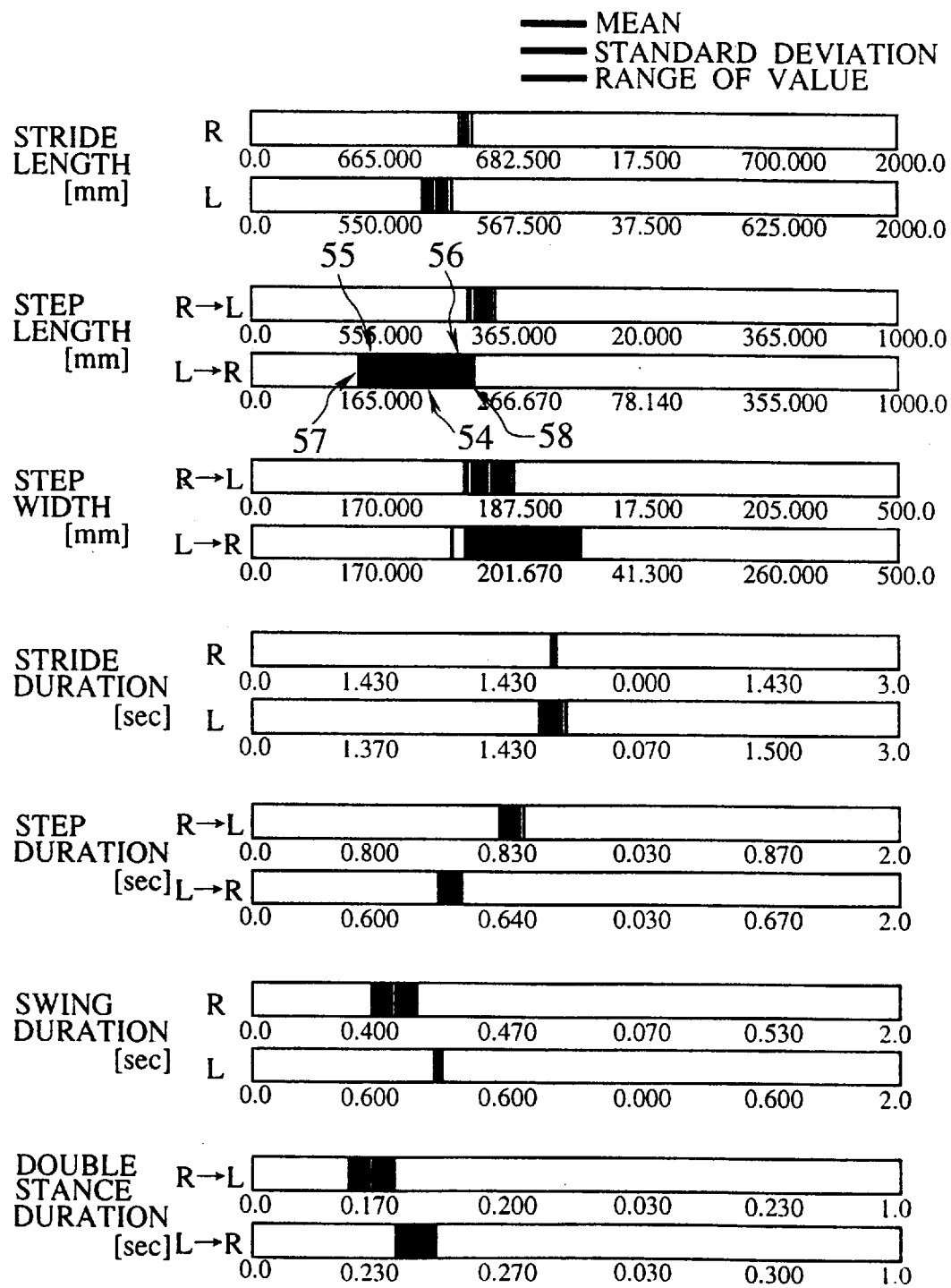
FIG. 11 is a view showing a display on which spatial parameters and time parameters concerning right and left feet are collated with each other.

FIG. 11 is a view showing a display on which spatial parameters and time parameters concerning right and left feet are collated with each other. For the right foot and the left foot, the walking parameter displaying portion 13 displays spatial parameters, i.e., stride length, step length, and step width, and time parameters, i.e., stride duration, step duration, swing duration, and double stance duration, detected by the feature location detecting portion 9 and the time interval detecting portion 12 by vertical lines. Since a plurality sets of parameters can be derived from plural steps of walking even if plural time walking or one time walking occurs, average value 54, average±standard deviation values 55, 56, maximum value 58, and minimum value 57 of these plurality sets of parameters can be displayed in different colors to overlap with each other.

An example of data of left hemiplegia patient is shown in FIG. 11. Especially, balance in right and left averages is affected in time parameters, and especially parameters on the hemiplegia (left) foot side are largely varied in spatial parameters.

Figure 12:
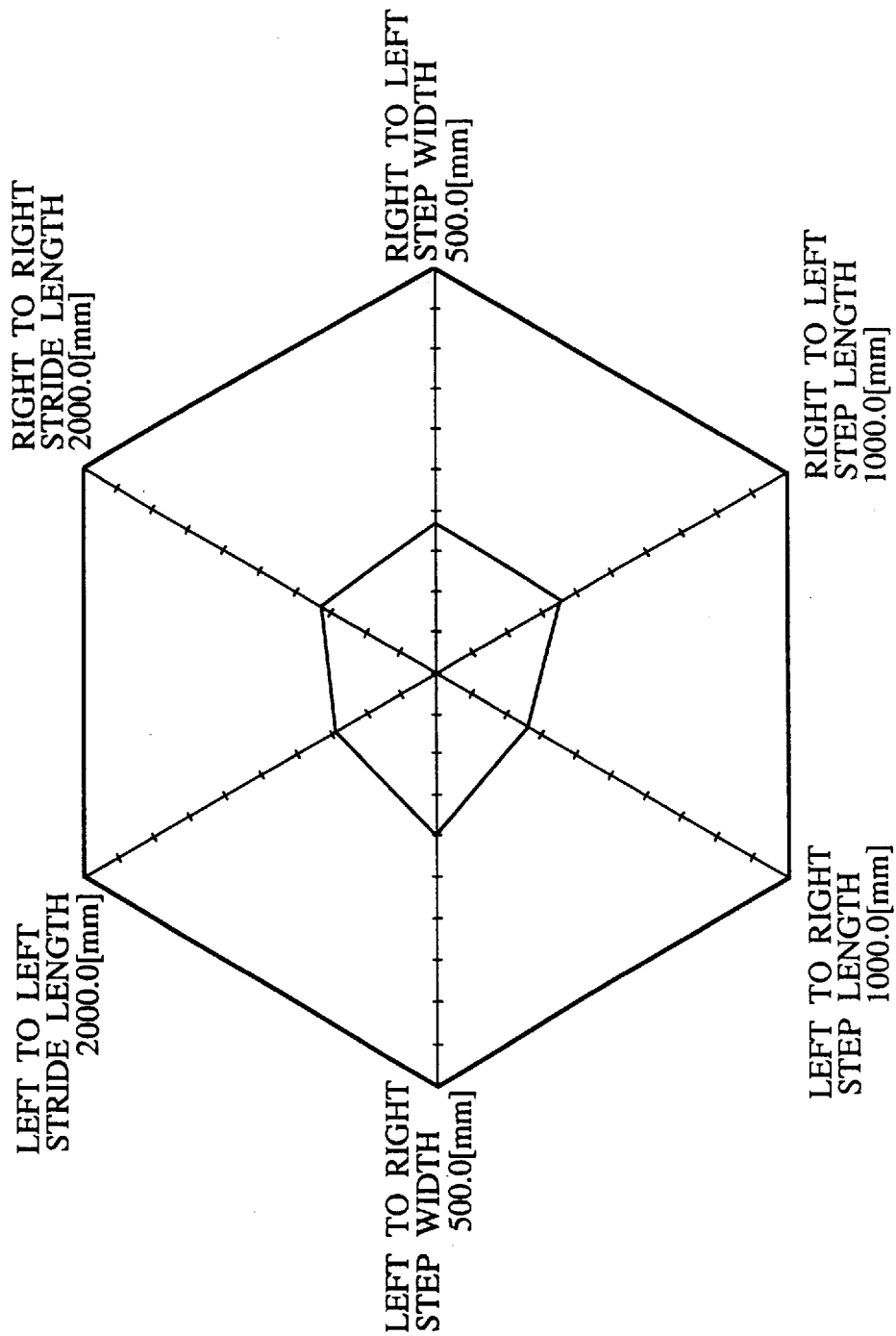
FIG. 12 is a view depicting an example of a radar chart of spatial parameters.

FIG. 12 is a view depicting an example of a radar chart of spatial parameters. The walking parameter displaying portion 13 displays spatial parameters, i.e., stride length, step length, and step width, detected by the feature location detecting portion 9 as the radar chart on respective feet. In this event, the step length and the stride length as lengths in the walking direction are selected as vertical parameters of the radar chart, whereas the step width as a length in the direction perpendicular to the walking direction is selected as a lateral parameter of the radar chart. Respective parameters associated with the right and left feet are arranged on the right and left location of the radar chart correspondingly. Thereby, the vertical/horizontal ratio and right/left balance of the radar chart indicate the walking pattern.

An example shown in FIG. 12 is data of left hemiplegia patient. Where it would be understood that the step and the stride of the left foot is small rather than those of the right foot.

Figure 13:
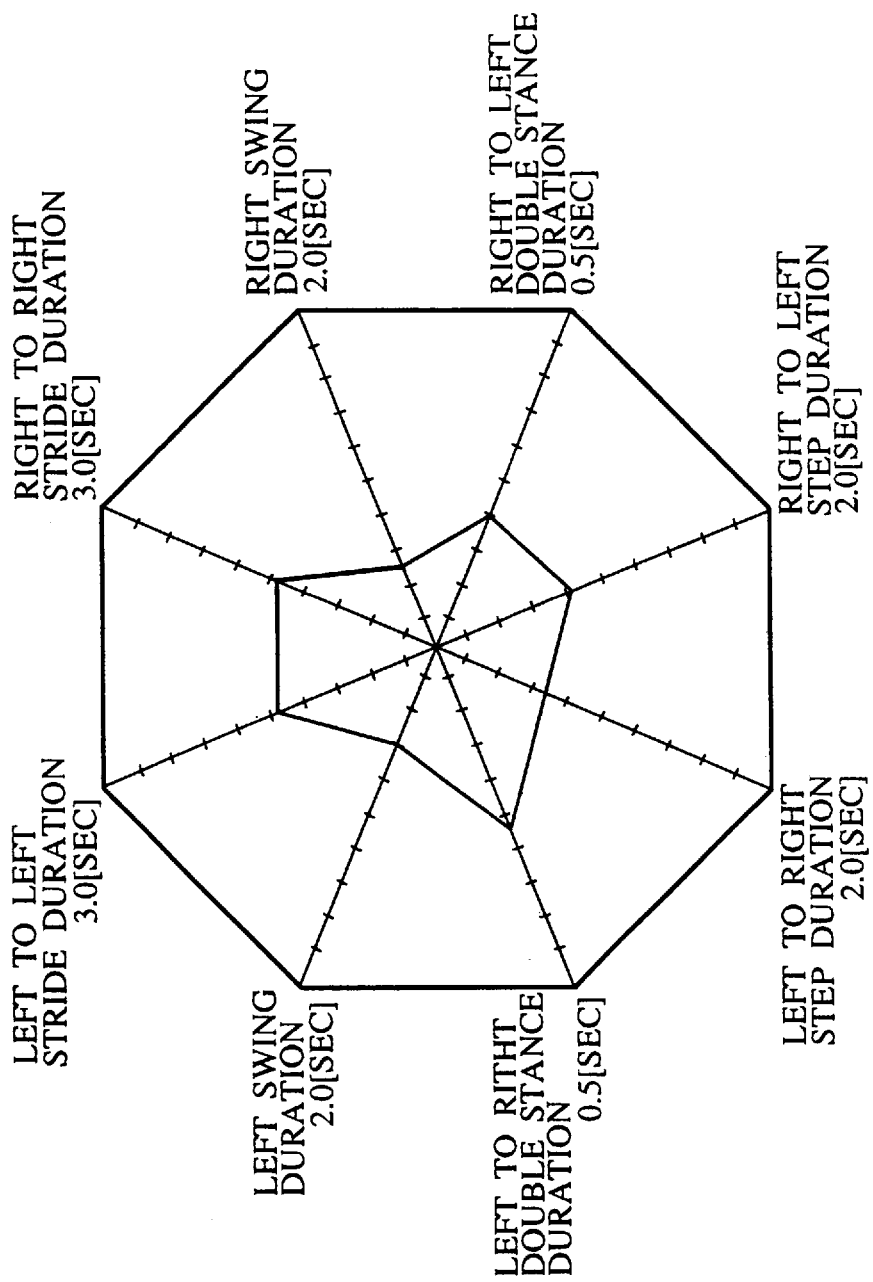
FIG. 13 is a view depicting an example of a radar chart of time parameters.

FIG. 13 is a view depicting an example of display of a radar chart concerning time parameters. The walking parameter displaying portion 13 displays time parameters, i.e., stride duration, step duration, swing duration, and double stance duration, detected by the time interval detecting portion 12 as the radar chart on respective feet. In this case, the times required for the step and the stride in the walking direction are selected as vertical parameters of the radar chart, whereas the double stance duration and the swing duration of the right foot and the left foot are selected as lateral parameters of the radar chart. Respective parameters associated with the right and left feet are arranged on the right and left location of the radar chart correspondingly. Thereby, the vertical/horizontal ratio and right/left balance of the radar chart indicate the walking pattern.

An example of data of left hemiplegia patient is shown in FIG. 13. As appreciated from FIG. 13, the double stance duration from the left to the right becomes extremely long, so that movement of the weight from the left to the right is difficult, i.e., kicking force of the left foot is insufficient.

According to the foregoing embodiments of the present invention, spatial and time parameters concerning walking actions can be collected automatically, stably, and simply without imposing a heavy burden on a subject. In addition, intuitive understanding and quantitative comparison of spatial and time factors of walking actions are facilitated. Hence, according to the embodiments of the present invention, effective application will be expected as follows.

(a) Measuring the degree of serious wound of diseases by which troubles are caused in the walking action in the medical field.

(b) Measuring the degree of progress of rehabilitation when such rehabilitation of the walking action is executed in the medical field.

(c) Measuring the effect of medicine which is effective to improvement in the walking action in the medical field by comparing conditions of the patient before and after such medicine is prescribed.

(d) Measuring the degree of serious wound by measuring the walking action of the patient who has no objective symptoms such as vertigo, waist ache, etc. in the medical field.

(e) According to the present invention, by collecting information of footprint location and time thereof detected stably together with images of the walking action and then utilizing these information together, walking action parameters such as angles of ankle joint, knee joint, hip joint, or the like can be detected stably.

It should be understood that many modifications and adaptations of the invention will become apparent to those skilled in the art and it is intended to encompass such obvious modifications and changes in the scope of the claims appended hereto.

What is claimed is:

1. A walking pattern processing method comprising the steps of:

collecting two-dimensional pressure distribution associated with walking at a preselected time interval as time series pressure distribution images;

forming superposed images by superposing said time series pressure distribution images in a time direction;

distinguishing a plurality of foot pressure mass regions one another to extract from said superposed images;

detecting correspondence of each foot pressure mass region to said time series pressure distribution images;

detecting feature parameters associated with said walking based on said correspondence; and displaying or printing said feature parameters.

2. A walking pattern processing method according to claim 1, wherein rear end portion, front end portion, and center in each step are detected as said feature parameters, and information as to a stride duration and a step duration are displayed or printed in parallel to said superposed images, and information as to a step width are displayed or printed so as to overlap with said superposed images.

3. A walking pattern processing method according to claim 1, wherein locations of said center of gravity of pressure values in each pressure distribution image are detected as said feature parameters, and detected locations of said center of gravity of pressure values in each pressure distribution image are displayed or printed in parallel to said superposed images.

4. A walking pattern processing method according to claim 3, wherein moving direction of said locations are detected upon detecting said locations of center of gravity of pressure values, and displaying or printing process is inverted if said center of gravity moves in a direction opposite to walking direction.

5. A walking pattern processing method according to claim 4, wherein colors used in said display or printing are changed if said center of gravity moves in a direction opposite to walking direction.

6. A walking pattern processing method according to claim 3, wherein said center of gravity is detected on each foot, and location of said center of gravity is displayed or printed.

7. A walking pattern processing method according to claim 3, wherein said center of gravity is detected on both feet, and location of said center of gravity is displayed or printed.

8. A walking pattern processing method according to claim 1, wherein said center of gravity of pressure distribution images having a pressure value firstly in each step is detected as said feature parameters, and location of said center of gravity is displayed or printed so as to overlap with said superposed images.

9. A walking pattern processing method according to claim 1, wherein stride duration, step duration, double stance duration, and swing duration are detected as said feature parameters, and foot contact times on both feet in connection with said stride duration, said step duration, said double stance duration, and said swing duration are displayed or printed by respective line segments along a time axis.

10. A walking pattern processing method according to claim 9, wherein sum total or an average value of said pressure values at respective time points is displayed or printed in different color or with different density so as to overlap with said line segments.

11. A walking pattern processing method according to claim 10, wherein a pressure level scale is displayed together with said line segments.

12. A walking pattern processing method according to claim 9, wherein said stride duration, said step duration, said double stance duration, and said swing duration are detected based on times of pressure distribution images having initial and final pressure values in each step.

13. A walking pattern processing method according to claim 1, wherein stride length, step length, step width, stride duration, step duration, double stance duration, and swing duration are detected as said feature parameters, and said stride length, said step length, said step width, said stride duration, said step duration, said double stance duration, and said swing duration are displayed or printed in scale so as to collate a right foot with a left foot.

14. A walking pattern processing method according to claim 5, wherein data concerning said stride length, said step length, said step width, said stride duration, said step duration, said double stance duration, and said swing duration are displayed or printed respectively, and average values, values of average value±standard deviation, maximum values and minimum values of these data are displayed or printed in different colors to overlap with said data.

15. A walking pattern processing method according to claim 1, wherein stride length, step length, and step width are detected as said feature parameters, and said stride length, said step length, and said step width are displayed or printed as a radar chart.

16. A walking pattern processing method according to claim 15, wherein said step length and said stride length which are lengths in a walking direction are selected as vertical parameters in said radar chart, and said step width which is a length in a direction perpendicular to said walking direction is selected as a lateral parameter in said radar chart, and respective parameters on right and left feet are arranged correspondingly on right and left sides of said radar chart.

17. A walking pattern processing method according to claim 1, wherein stride duration, step duration, double stance duration, and swing duration are detected as said feature parameters, and said stride duration, said step duration, said double stance duration, and said swing duration are displayed or printed as a radar chart.

18. A walking pattern processing method according to claim 17, wherein time required for step and stride actions in a walking direction are selected as vertical parameters in said radar chart, and said double stance duration and said swing duration on a right foot and a left foot are selected as lateral parameters in said radar chart, and respective parameters on right and left feet are arranged correspondingly on right and left sides of said radar chart.

\* \* \* \* \*